United States Patent
Kargar et al.

(10) Patent No.: US 7,889,841 B2
(45) Date of Patent: *Feb. 15, 2011

(54) X-RAY IMAGING SYSTEM FOR PERFORMING AUTOMATED MULTI-STEP IMAGING OF PATIENT ANATOMY

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 253 days.

This patent is subject to a terminal disclaimer.

(21) Appl. No.: 12/366,277

(22) Filed: Feb. 5, 2009

(65) Prior Publication Data

US 2009/0238331 A1 Sep. 24, 2009

Related U.S. Application Data

(60) Provisional application No. 61/052,762, filed on May 13, 2008, provisional application No. 61/052,320, filed on May 12, 2008, provisional application No. 61/051,771, filed on May 9, 2008, provisional application No. 61/037,424, filed on Mar. 18, 2008, provisional application No. 61/037,420, filed on Mar. 18, 2008.

(51) Int. Cl.
*G01N 23/04* (2006.01)
(52) U.S. Cl. ............................ 378/62; 378/196; 378/197
(58) Field of Classification Search .................... 378/62, 378/91, 95, 196, 197, 158, 98.12

See application file for complete search history.

(56) References Cited

U.S. PATENT DOCUMENTS

| | | | |
|---|---|---|---|
| 4,744,099 A | 5/1988 | Huettenrauch et al. | |
| 5,917,882 A | 6/1999 | Khutoryansky et al. | |
| 5,917,883 A | 6/1999 | Khutoryansky et al. | |
| 6,584,173 B2 | 6/2003 | Zwarf et al. | |
| 6,980,623 B2 | 12/2005 | Dunhan et al. | |
| 7,340,033 B2 | 3/2008 | Mollus et al. | |
| 7,344,305 B2 | 3/2008 | Kuzmanovic | |
| 7,734,007 B2 * | 6/2010 | Kargar et al. | 378/8 |
| 2002/0051516 A1 | 5/2002 | Zwarf et al. | |
| 2006/0203966 A1 | 9/2006 | Mollus et al. | |
| 2008/0025586 A1 | 1/2008 | Baumgart et al. | |
| 2008/0037708 A1 | 2/2008 | Kuzmanovic | |

* cited by examiner

*Primary Examiner*—Jurie Yun
(74) *Attorney, Agent, or Firm*—Alexander J Burke

(57) ABSTRACT

An X-ray imaging system performs automated multi-step imaging of patient anatomy and includes an X-ray imaging device. The X-ray imaging device supports automated movement of an X-ray detector and X-ray emitter combination relative to patient anatomy in a series of pre-programmed steps. A multi-step programming interface enables a user to select, (a) a start position for X-ray imaging at a first location of a portion of patient anatomy and (b) an end position for X-ray imaging at a second location of a portion of patient anatomy. A computation processor automatically determines a series of pre-programmed steps comprising multiple incremental distances to be moved by the X-ray detector and X-ray emitter combination relative to the portion of patient anatomy in response to predetermined data including, (i) the selected start and end positions, (ii) the length of the portion of patient anatomy imaged in an individual step and (iii) the amount of overlap desired between successive X-ray images. An imaging controller initiates automated multi-step imaging of the portion of patient anatomy by the X-ray imaging device in response to data representing the determined series of pre-programmed steps and user command.

18 Claims, 5 Drawing Sheets

X-RAY IMAGING SYSTEM FOR PERFORMING AUTOMATED MULTI-STEP IMAGING OF PATIENT ANATOMY

This is a non-provisional application of provisional application Ser. No. 61/037,420 filed Mar. 18, 2008, provisional application Ser. No. 61/037,424 filed Mar. 18, 2008, provisional application Ser. No. 61/051,771 filed May 9, 2008, provisional application Ser. No. 61/052,320 filed May 12, 2008 and provisional application Ser. No. 61/052,762 filed May 13, 2008, by S. Kargar et al.

FIELD OF THE INVENTION

This invention concerns an X-ray imaging system for performing automated multi-step imaging of patient anatomy by automatically determining steps an X-ray device is to be moved and automatically adjusting X-ray radiation attenuation filters.

BACKGROUND OF THE INVENTION

In performing X-ray imaging angiography of the lower limbs of a patient, imaging usually starts at the pelvis and ends at the foot. The size of an imaging system X-ray radiation detector dictates image size. Thus, several images are acquired in a sequence of steps in order to cover an entire limb. The acquired images are joined (e.g., sewn) together and the entire limb image is created if so desired. Since each image is of a different part of the body, X-ray absorption differs in each X-ray imaging step. The X-ray radiation needs to be regulated and optimized for optimum image quality for individual steps.

In known systems, Peripheral Angiography workflow involves many user interactions. A user first performs X-ray imaging in individual steps (e.g., from the pelvis to the foot) on the patient lower limbs for configuration and to manually adjust a collimator, semi-transparent filters and finger filters for each step. A collimator narrows an X-Ray beam to cause the spatial cross section of the beam to become smaller and comprises individual plates or a diaphragm or system of diaphragms made of an absorbent material and arranged to determine the dimensions and direction of an X-ray beam of radiation. Semi-transparent filters attenuate particular (or all) wavelengths of X-ray radiation provided from a radiation source collimator to a portion of a patient and a finger filter attenuates substantially all X-ray radiation provided from a radiation source collimator to a portion of a patient.

A user further performs X-ray imaging in individual steps on the patient lower limbs (from foot to pelvis) to determine a mask for subtraction of background detail. A third X-ray imaging pass is performed in individual steps on the patient lower limbs (from foot to pelvis), following injection of an X-ray contrast agent into the patient, to obtain desired X-ray images. In moving through the sequence of steps, the forward speed of movement of an X-ray source and detector combination relative to a patient table, is controlled by a user via a switch, for example. Known X-ray imaging of the limbs is cumbersome, involving multiple imaging passes and multiple steps as well as manual adjustment of a collimator, semi-transparent filters and finger filters for each individual step. A system according to invention principles automates a substantial portion of the process and addresses associated problems.

SUMMARY OF THE INVENTION

A system performs automated multi-step imaging of patient anatomy by automatically determining steps an X-ray device is to be moved and automatically adjusting an X-ray radiation attenuation filter. An X-ray imaging system performs automated multi-step imaging of patient anatomy and includes an X-ray imaging device. The X-ray imaging device supports automated movement of an X-ray detector and X-ray emitter combination relative to patient anatomy in a series of pre-programmed steps. A multi-step programming interface enables a user to select, (a) a start position for X-ray imaging at a first location of a portion of patient anatomy and (b) an end position for X-ray imaging at a second location of a portion of patient anatomy. A computation processor automatically determines a series of pre-programmed steps comprising multiple incremental distances to be moved by the X-ray detector and X-ray emitter combination relative to the portion of patient anatomy in response to, (i) the selected start and end positions, (ii) the length of the portion of patient anatomy imaged in an individual step and (iii) the amount of overlap desired between successive X-ray images. An imaging controller initiates automated multi-step imaging of the portion of patient anatomy by the X-ray imaging device in response to data representing the determined series of pre-programmed steps and user command.

DETAILED DESCRIPTION OF THE INVENTION

Figure 1:
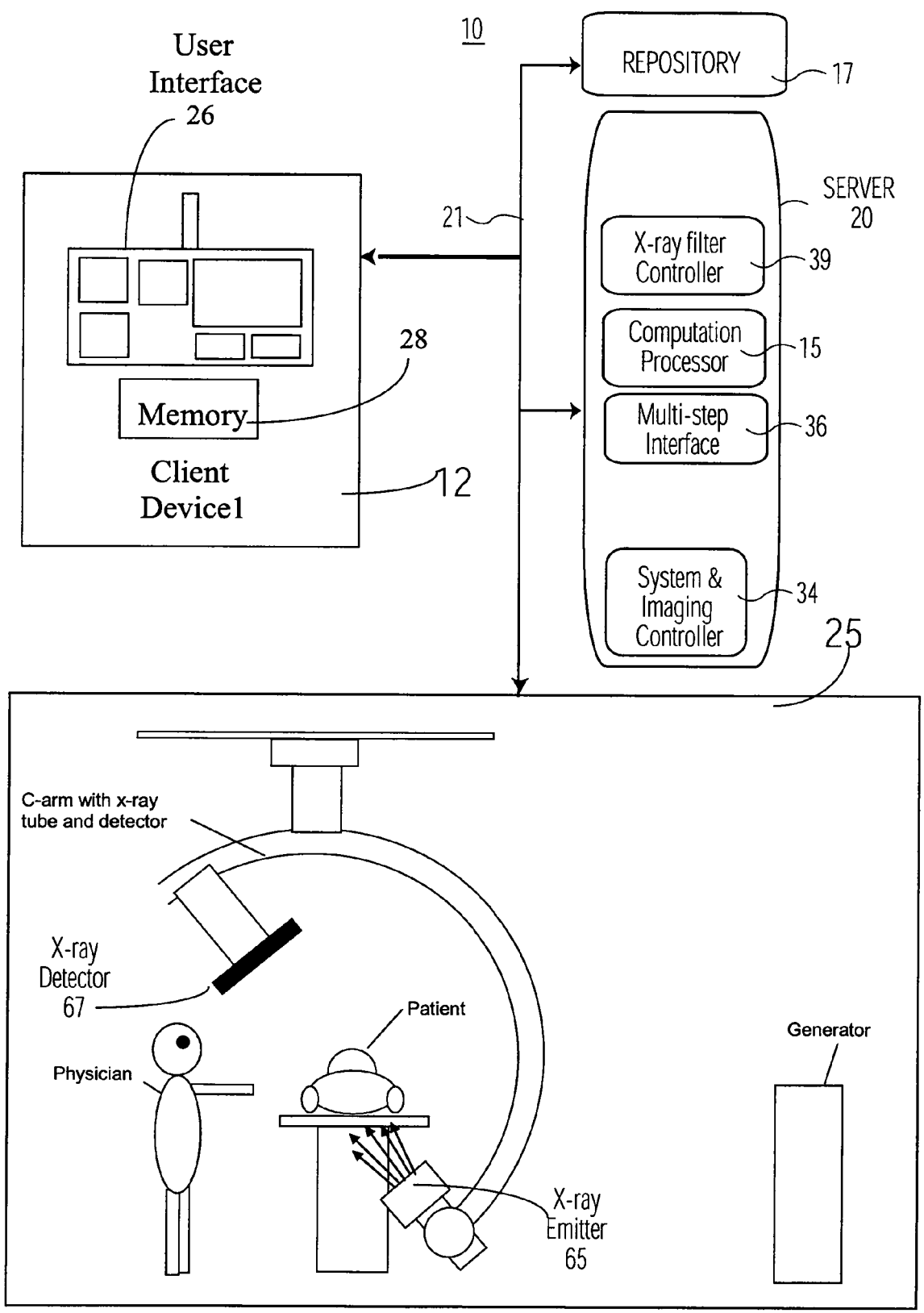
FIG. 1 shows an X-ray imaging system for performing automated multi-step imaging of patient anatomy, according to invention principles.

A system performs automated multi-step imaging of patient anatomy by automatically determining steps an X-ray device is to be moved and automatically adjusting an X-ray radiation attenuation filter. The system streamlines Peripheral digital Angiography workflow, e.g., of patient limbs, by automatically calculating the number of steps needed for an X-ray imaging procedure and by automatically adjusting X-ray attenuation filters. A user initiates performance of three X-ray imaging passes of one or more patient limbs, for example. These passes include a first fluoroscopy imaging pass for configuration and adjustment of X-ray emitter and detector characteristics, a second imaging pass for determining a mask image and a third imaging pass following injection of a contrast agent, to obtain digitally subtracted images of patient limbs, for example. Individual imaging passes involve multiple imaging steps through predetermined imaging positions to cover the full length of limbs. Further, in known systems in performing the first, second and third imaging passes, a user initiates movement of a radiation emitter and detector (e.g., mounted on a C-arm) relative to a patient table, to the predetermined imaging positions and manually adjusts a collimator, semi-transparent filter and finger filters (X-ray filters) for individual steps of at least one of the three imaging passes. The movement of the radiation emitter and detector on a C-arm, for example, or patient table may be controlled via joystick control. A system according to invention principles automates the repetitive steps to involve minimum user interaction.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

FIG. 1 shows X-ray imaging system 10 for performing automated multi-step imaging of patient anatomy. System 10 includes one or more processing devices (e.g., workstations, computers or portable devices such as notebooks, Personal Digital Assistants, phones) 12 that individually include memory 28 and a user interface 26 supporting image presentation in response to predetermined user (e.g., physician) specific preferences. System 10 also includes at least one repository 17, X-ray imaging modality system 25 and server 20 intercommunicating via network 21. User interface 26 provides data representing display images comprising a Graphical User Interface (GUI) for presentation on processing device 12. At least one repository 17 stores medical image studies for multiple patients in DICOM compatible (or other) data format. A medical image study individually includes multiple image series of a patient anatomical portion which in turn individually include multiple images. Server 20 includes, computation processor 15, X-ray filter controller 39, multi-step programming interface 36 and system and imaging controller 34. At least one repository 17 also includes predetermined data comprising, (a) a start position for X-ray imaging at a first location of a portion of patient anatomy and (b) an end position for X-ray imaging at a second location of a portion of patient anatomy. The predetermined data also comprises, (i) selected start and end positions for X-ray imaging the length of a portion of patient anatomy, (ii) the length of the portion of patient anatomy imaged in an individual step and (iii) overlap length desired between successive X-ray images.

X-ray imaging system 10 performs automated multi-step imaging for use in Peripheral Angiography of patient limbs such as legs, for example. X-ray imaging device 25 supports automated movement of an X-ray detector 67 and X-ray emitter 65 combination mounted on a C-arm, for example, relative to patient anatomy in a series of pre-programmed steps. X-ray emitter 65 includes a collimator, semi-transparent filters and an X-ray filter (finger filter) automatically adjustable to attenuate X-ray radiation in response to a control signal. The X-ray filter is located substantially close to X-ray emitter 65 to attenuate X-ray radiation from X-ray emitter 65 before it passes through a patient. Multi-step programming interface 36 enables a user to select, (a) a start position for X-ray imaging at a first location of a portion of patient anatomy and (b) an end position for X-ray imaging at a second location of a portion of patient anatomy. The movable arm is movable to the start and end positions in response to user interaction and user interface 26 enables a user to select the start and end positions following movement of the arm and the X-ray detector 67 and X-ray emitter 65 combination relative to the portion of patient anatomy to the start and end positions respectively. X-ray imaging device 25 also includes a generator for providing power (such as high voltage power) for powering the X-ray emitter, for example.

Computation processor 15 (at least one computer) automatically determines a series of pre-programmed steps comprising multiple incremental distances to be moved by the X-ray detector 67 and X-ray emitter 65 combination relative to the portion of patient anatomy in response to, (i) the selected start and end positions, (ii) the length of the portion of patient anatomy imaged in an individual step, (iii) the amount of overlap desired between successive X-ray images and (iv) the area of the portion of patient anatomy imaged in an individual step. The length of the portion of patient anatomy imaged in an individual step is determined in response to an imaging zoom factor and the size of an imaging X-ray detector. Computation processor 15 automatically determines the multiple incremental distances by dividing a distance between the start and end positions by a distance moved by the X-ray detector 67 and X-ray emitter 65 combination relative to the portion of patient anatomy in an individual step. The distance moved by the X-ray detector 67 and X-ray emitter 65 combination relative to the portion of patient anatomy in an individual step is determined by subtracting a distance representing the overlap desired between successive X-ray images. Imaging controller 34 initiates automated multi-step imaging of the portion of patient anatomy by X-ray imaging device 25 in response to data representing the determined series of pre-programmed steps and user command.

X-ray filter controller 39, identifies one or more areas of the X-ray detector 67 exposed to X-ray radiation un-attenuated by patient anatomy during an initialization exposure for individual steps of the series of pre-programmed steps. Controller 39 determines different positions of an X-ray filter automatically adjustable to attenuate X-ray radiation for corresponding individual steps of the series of pre-programmed steps in response to the identified one or more areas. Controller 39 automatically adjusts the X-ray filter position to the determined X-ray filter positions to attenuate X-ray radiation un-attenuated by patient anatomy for individual steps of the series of pre-programmed steps, in response to data representing the determined different positions.

Figure 2:
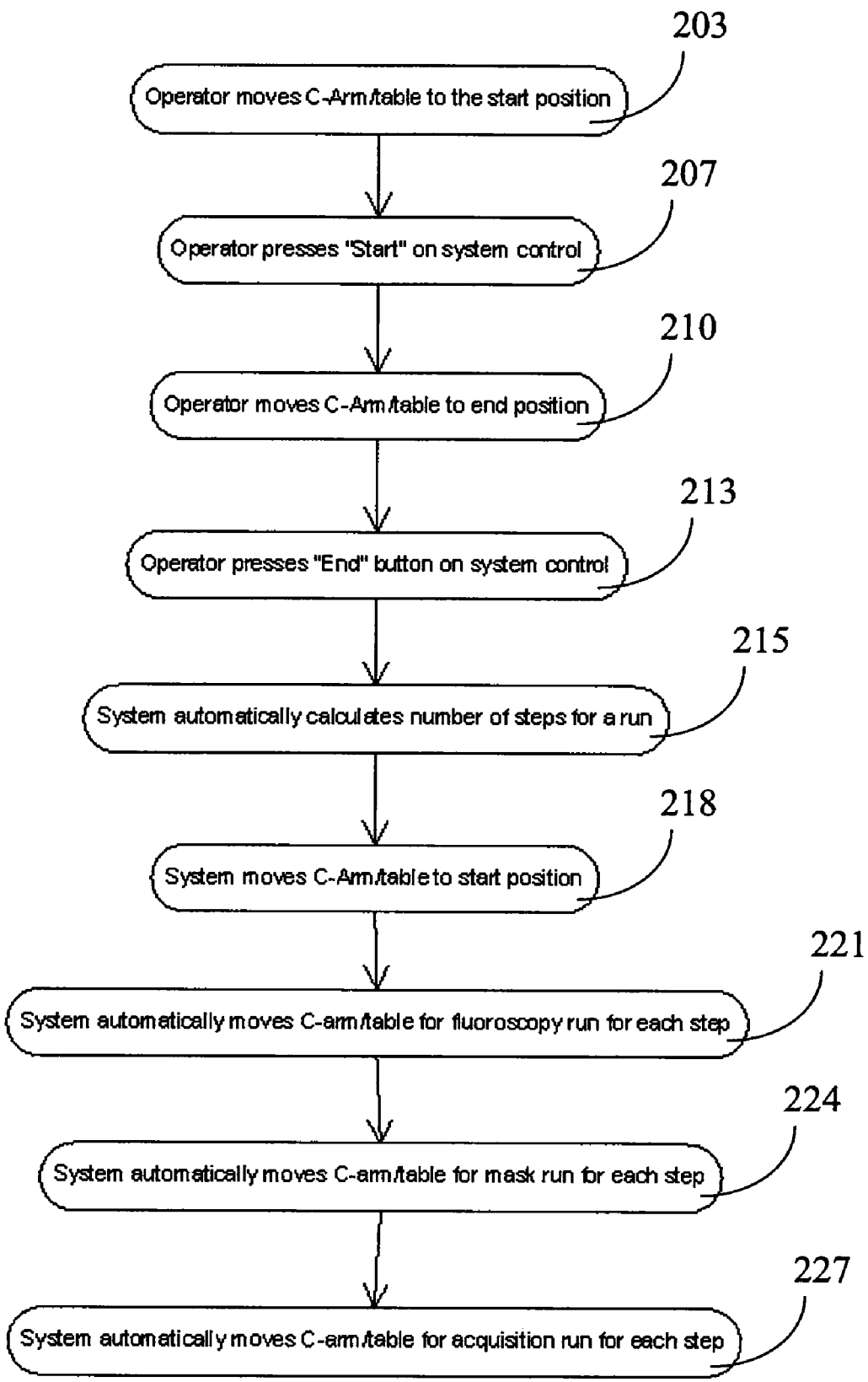
FIG. 2 shows a flowchart of a process performed by an X-ray imaging system for performing automated multi-step imaging of patient anatomy, according to invention principles.

FIG. 2 shows a flowchart of a process performed by X-ray imaging system 10 (FIG. 1) for performing automated multi-step imaging of patient anatomy. In step 203, a user employing multi-step programming interface 36 and controller 34, initiates automated movement of an X-ray detector 67 and X-ray emitter 65 combination mounted on a C-arm to a start position such as the pelvis when imaging lower limbs. In step 207 interface 36 records the start position arm location in response to user command. In step 210, a user employing multi-step programming interface 36 and controller 34, initiates automated movement of the X-ray detector 67 and X-ray emitter 65 combination to an end position such as the feet. In step 213 interface 36 records the end position arm location, in response to user command. In step 215, computation processor 15 automatically determines a series of pre-programmed steps comprising multiple incremental distances to be moved by the X-ray detector 67 and X-ray emitter 65 combination relative to the portion of patient anatomy from the selected start position to the end position. Computation processor 15 automatically calculates the number of pre-programmed steps needed for use in each of three X-ray imaging passes (i.e., configuration, mask determination and imaging passes) and a user drives the C-arm or patient table to the start and end position.

Computation processor 15 processes the start and end position information and calculates the number of pre-programmed steps needed for the X-ray imaging pass. The number of steps is obtained by dividing the distance between the start and end positions by the selected zoom size. For instance, the distance between the pelvis and the foot of a patient is 72 cm and the zoom factor 2 i.e. 32 cm is selected. The numbers of steps are calculated by processor 15 as follows, Zoom factor 2 corresponds to a 22×22 cm area being covered by X-ray radiation detector 67. Overlap between each imaging step is 4 cm therefore, 22−4=18 cm is the distance traveled in each pre-programmed step by the X-ray detector 67 and X-ray emitter 65 combination relative to patient anatomy and 72/18=4 is the Number of pre-programmed steps needed to cover the limb.

In step 218 imaging controller 34 initiates movement of the X-ray detector 67 and X-ray emitter 65 combination on a C-arm, for example, to the start position and initiates a process of automatically moving the C-arm or a patient table for the individual pre-programmed steps for the three X-ray image acquisition passes (configuration, mask determination and imaging passes). In step 221, controller 34 automatically moves the C-arm or a patient table for the individual pre-programmed steps of a configuration (a fluoroscopy) imaging pass. A user needs to adjust the X-ray filter, collimator and semi-transparent filter in individual pre-programmed steps of the configuration imaging pass. In contrast in known systems a user typically needs to adjust the X-ray filter, collimator and semi-transparent filter in individual pre-programmed steps for each of the configuration pass, mask determination pass and imaging pass. In a further embodiment, the system automatically adjusts the X-ray filter without need for manual X-ray filter adjustment at all. In step 224, controller 34 automatically moves the C-arm or a patient table for the individual pre-programmed steps of a mask determination imaging pass and in step 227, controller 34 automatically moves the C-arm or a patient table for the individual pre-programmed steps of an imaging pass, e.g., in the presence of a contrast agent to obtain digitally subtracted images of patient limbs.

Figure 3:
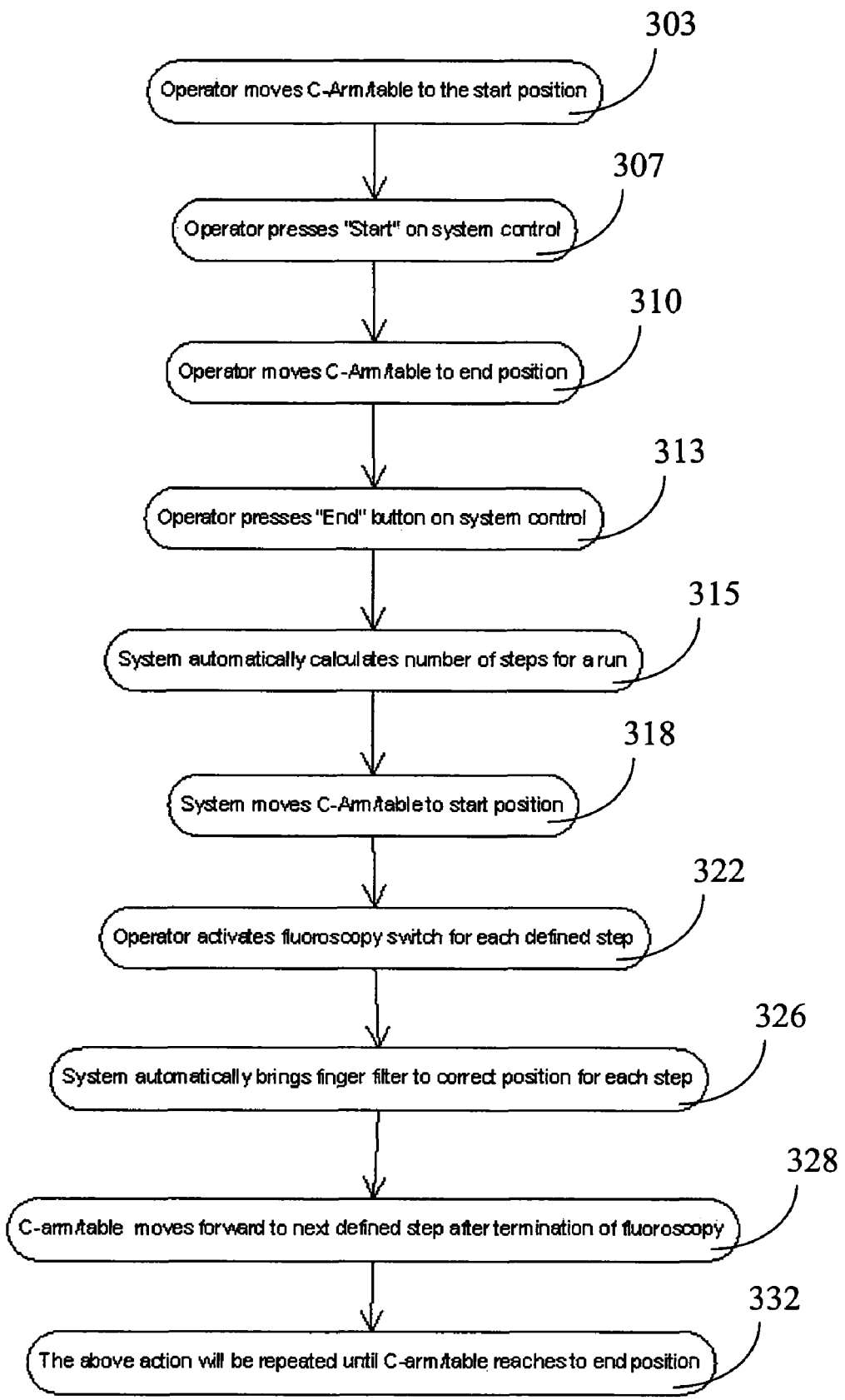
FIG. 3 shows a flowchart of a process performed by an X-ray imaging system for performing automated multi-step imaging of patient anatomy and automated filter adjustment, according to invention principles.

FIG. 3 shows a flowchart of a process performed by X-ray imaging system 10 (FIG. 1) for performing automated multi-step imaging of patient anatomy and automated X-ray filter adjustment. System 10 performs steps 303, 307, 310, 313 and 315 as previously described in connection with corresponding steps 203, 207, 210, 213 and 215 of FIG. 2. In step 318 imaging controller 34 initiates movement of the X-ray detector 67 and X-ray emitter 65 combination on a C-arm, for example, to a start position and initiates a process of automated X-ray filter adjustment. An automatically adjustable X-ray filter attenuates X-ray radiation being emitted that does not pass through patient anatomy and merely passes between the legs of a patient, for example. This facilitates compensation for the absence of tissue in a radiation detector output signal to improve X-ray imaging contrast of displayed anatomical detail. The X-ray filter in the X-ray emitter 65 unit of X-ray imaging unit 25 is automatically adjustable to attenuate X-ray radiation in response to a control signal. Specifically, the X-ray filter is automatically adjusted to a filter position for lower (or upper limb) angiography in response to detection by the X-ray detector of an area of raw radiation. In step 322, controller 34 automatically moves the C-arm or a patient table for the individual pre-programmed steps of a configuration (a fluoroscopy) imaging pass. In step 326, X-ray filter controller 39 automatically adjusts the X-ray filter to attenuate X-ray radiation passing external to patient anatomy, for the individual pre-programmed steps of the configuration imaging pass.

Figure 4:
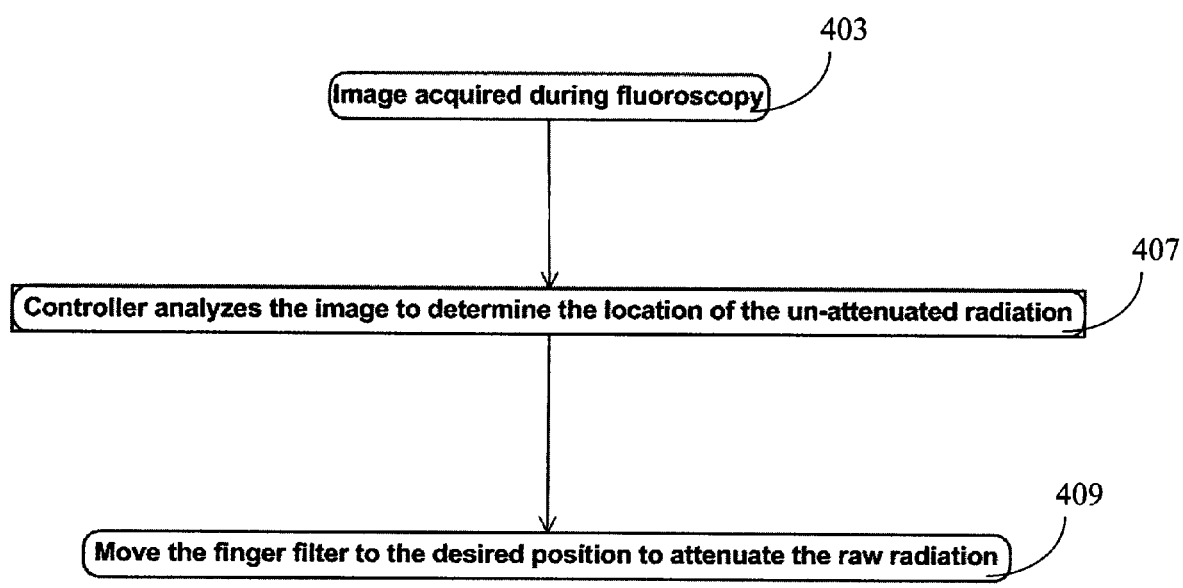
FIG. 4 shows a flowchart of a process performed by an X-ray imaging system for performing automated filter adjustment, according to invention principles.

FIG. 4 shows a flowchart of a process performed by X-ray imaging unit 25 (FIG. 1) for performing automated filter adjustment. In the initialization (configuration) imaging pass of step 403, X-ray filter controller 39 in step 407 determines one or more areas of the X-ray detector 67 of system 25 exposed to X-ray radiation un-attenuated by patient anatomy (e.g., an area filled with air between patient legs). This is done for individual steps of the series of pre-programmed steps. X-ray filter controller 39 determines different positions of the automatically adjustable X-ray filter to attenuate X-ray radiation for corresponding individual steps of the series of pre-programmed steps in response to the determined areas.

Thereby, X-ray imaging system 25 advantageously improves image quality of the lower limbs for the individual pre-programmed steps by improving X-ray imaging contrast of displayed anatomical detail. Determining location of received raw radiation in the radiation detector 67 may be performed in different ways. In one embodiment, controller 39 derives a histogram representing image brightness of multiple individual pixels and identifies raw radiation in response to histogram luminance representative levels exceeding a predetermined threshold. Thereby a histogram is used to locate a distribution of raw radiation. An area with no dark pixels or few dark pixels, for example, as indicated by a pixel luminance threshold detector is identified as an area of raw radiation. In response to detection of a raw radiation area, controller 39 commands the X-ray filter in step 409 to move to a desired position. Controller 39 automatically adjusts the X-ray filter position to the determined X-ray filter positions to attenuate X-ray radiation un-attenuated by patient anatomy for individual steps of the series of pre-programmed steps, in response to data representing the determined different positions. In another embodiment a closed loop feedback loop is used to move the X-ray filter and minimize an area of raw radiation detected by detector 67.

Continuing with FIG. 3, in step 328, controller 34 automatically moves the C-arm or a patient table for the individual pre-programmed steps of a mask determination imaging pass and similarly automatically moves the C-arm or a patient table for the individual pre-programmed steps of an imaging pass, e.g., in the presence of a contrast agent to obtain digitally subtracted images of patient limbs. In similar fashion to that described in connection with steps 322 and 326, the X-ray filter is automatically adjusted for the individual pre-programmed steps of the mask determination and imaging passes. The process of FIG. 3 ends in step 332.

Figure 5:
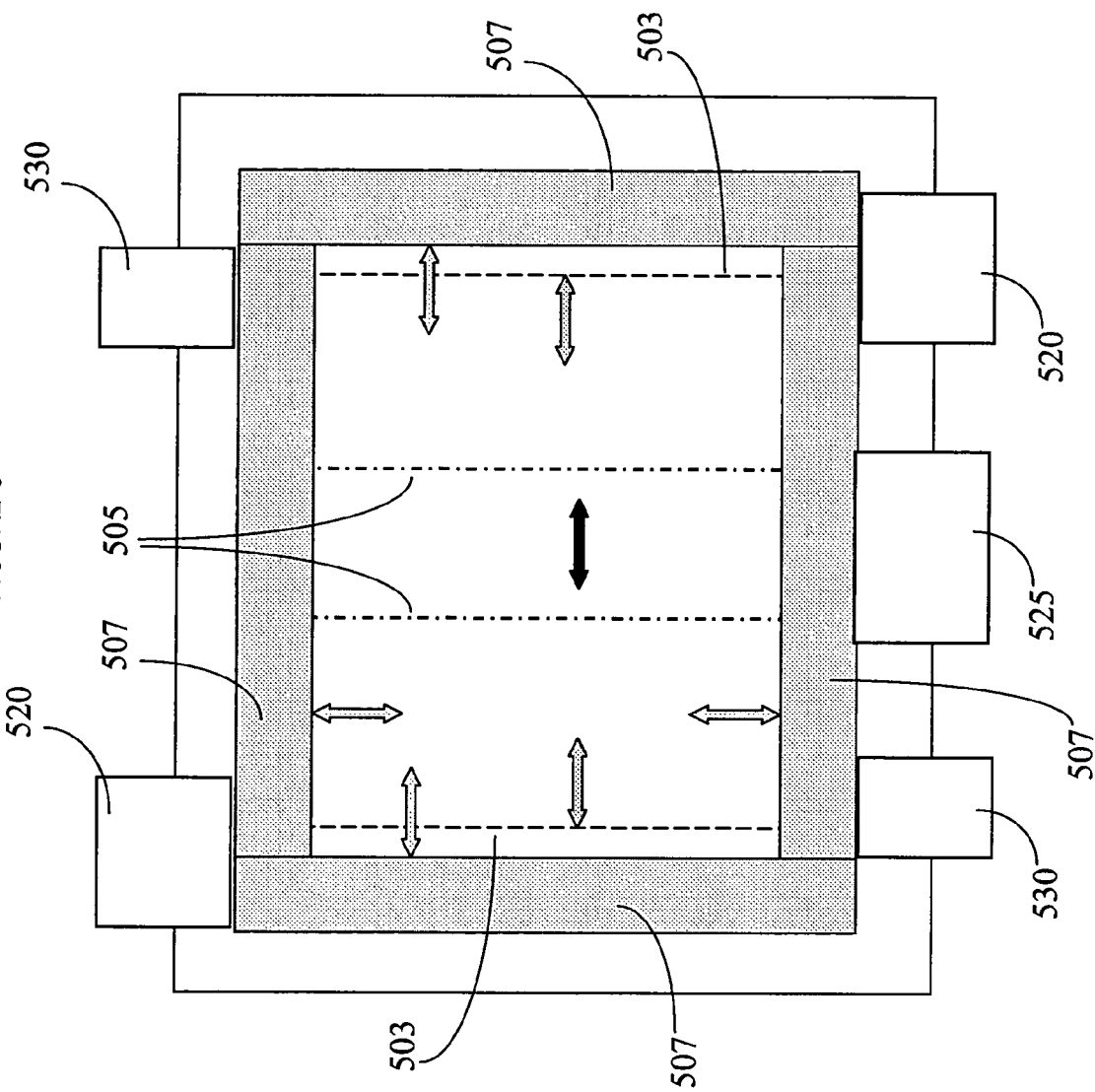
FIG. 5 shows an adjustable collimator, semi-transparent filters and finger filters mounted in an X-ray radiation emitter unit, according to invention principles.

FIG. 5 shows an adjustable unit comprising automatically adjustable collimator, semi-transparent filters and X-ray (finger filter) mounted in an X-ray radiation emitter 65 unit of X-ray imaging unit 25. The adjustable collimator comprises plates 507 automatically individually movable by actuators 520 (e.g., stepper motors) to expand or reduce X-ray beam cross-section and determine an X-ray field of view, in response to a control signal provided by controller 39 (FIG. 1). The adjustable semi-transparent filter comprises semi-transparent filters 503 automatically individually movable by actuators 530 (e.g., stepper motors) to expand or reduce a portion of the X-ray beam that is attenuated in response to a control signal provided by controller 39. The semi-transparent filter is adjusted to compensate for tissue density variation resulting in difference in X-ray attenuation of different parts of anatomy such as a leg (X-ray attenuation of the middle part of a leg including bone is typically greater than the sides of the leg). The adjustable X-ray filter comprises plates 505 automatically individually movable by actuator 525 (e.g., a stepper motor) to expand or reduce a portion of the X-ray beam that is attenuated in response to a control signal provided by controller 39 derived in response to detection by the X-ray detector 67 of an area of raw radiation. Controller 39 moves the X-ray filter to attenuate radiation that passes between patient legs, for example, to compensate for absence of tissue. In other embodiments, the adjustable collimator, semi-transparent filters and X-ray filter may comprise different adjustable plates and attenuation materials involving different geometries, shapes, sizes and angles.

The systems and processes of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system provides automatic calculation of the number of steps involved in peripheral angiography and imaging of body parts or objects that require multiple frames to be sewn together to get a complete picture of the object. The system provides automatic positioning of an X-ray filter (e.g., to block radiation from passing to the area between legs). Further, the processes and applications may, in alternative embodiments, be located on one or more (e.g., distributed) processing devices. Any of the functions and steps provided in FIGS. 1-5 may be implemented in hardware, software or a combination of both.

What is claimed is:

1. An X-ray imaging system for performing automated multi-step imaging of patient anatomy, comprising:
   an X-ray imaging device supporting automated movement of an X-ray detector and X-ray emitter combination relative to patient anatomy in a series of pre-programmed steps;
   a multi-step programming interface enabling a user to select,
     (a) a start position for X-ray imaging at a first location of a portion of patient anatomy and
     (b) an end position for X-ray imaging at a second location of a portion of patient anatomy;
   a computation processor for automatically determining a series of pre-programmed steps comprising a plurality of incremental distances to be moved by said X-ray detector and X-ray emitter combination relative to said portion of patient anatomy in response to,
     (i) the selected start and end positions,
     (ii) the length of said portion of patient anatomy imaged in an individual step and
     (iii) the amount of overlap desired between successive X-ray images; and
   an imaging controller for initiating automated multi-step imaging of said portion of patient anatomy by said X-ray imaging device in response to data representing the determined series of pre-programmed steps and user command.

2. A system according to claim 1, wherein
   said X-ray detector and X-ray emitter combination are mounted on a movable arm and the arm is moved through said series of pre-programmed steps.

3. A system according to claim 2, wherein
   said movable arm is movable to said start and end positions in response to user interaction and including
   a user interface enabling a user to select said start and end positions following movement of said arm to said start and end positions respectively.

4. A system according to claim 1, wherein
   said computation processor automatically determines said series of pre-programmed steps in response to the area of said portion of patient anatomy imaged in an individual step.

5. A system according to claim 1, wherein
   said computation processor automatically determines said plurality of incremental distances by dividing a distance between said start and end positions by a distance moved by said X-ray detector and X-ray emitter combination relative to said portion of patient anatomy in an individual step.

6. A system according to claim 5, wherein
said distance moved by said X-ray detector and X-ray emitter combination relative to said portion of patient anatomy in an individual step is determined by subtracting a distance representing the overlap desired between successive X-ray images.

7. A system according to claim 1, wherein
the length of said portion of patient anatomy imaged in an individual step is determined in response to an imaging zoom factor and the size of the X-ray detector.

8. A sytem according to claim 1, including
a user interface enabling a user to select said start and end positions following movement of said X-ray detector and X-ray emitter combination relative to said portion of patient anatomy to said start and end positions respectively.

9. A system according to claim 1, including
an X-ray filter controller for,
   identifying one or more areas of the X-ray detector exposed to X-ray radiation un-attenuated by patient anatomy during an initialization X-ray exposure for individual steps of said series of pre-programmed steps,
   determining different positions of an X-ray filter automatically adjustable to attenuate X-ray radiation for corresponding individual steps of said series of pre-programmed steps in response to the identified one or more areas and
   automatically adjusting the X-ray filter position to the determined X-ray filter positions to attenuate X-ray radiation un-attenuated by patient anatomy for individual steps of said series of pre-programmed steps, in response to data representing the determined different positions.

10. A method used by an X-ray imaging system for performing automated multi-step imaging of patient anatomy, comprising the activities of:
   storing data representing selected positions including,
      (a) a start position for X-ray imaging at a first location of a portion of patient anatomy and
      (b) an end position for X-ray imaging at a second location of a portion of patient anatomy;
   automatically determining a series of pre-programmed steps comprising a plurality of incremental distances to be moved by an X-ray detector and X-ray emitter combination relative to said portion of patient anatomy in response to,
      (i) the selected start and end positions,
      (ii) the length of said portion of patient anatomy imaged in an individual step and
      (iii) overlap length desired between successive X-ray images; and
   automatically moving the X-ray detector and X-ray emitter combination relative to patient anatomy in the series of pre-programmed steps, in response to data representing the determined series of pre-programmed steps and user command.

11. A method according to claim 10, including the activity of
   enabling a user employing a user interface, to select said start and end positions following movement of said X-ray detector and X-ray emitter combination relative to said portion of patient anatomy to said start and end positions respectively.

12. A method according to claim 10, wherein
said portion of patient anatomy is a patient limb.

13. A method according to claim 10, including the activities of
   determining one or more areas of the X-ray detector exposed to X-ray radiation un-attenuated by patient anatomy during an initialization X-ray exposure for individual steps of said series of pre-programmed steps,
   determining different positions of an X-ray filter automatically adjustable to attenuate X-ray radiation for corresponding individual steps of said series of pre-programmed steps in response to the determined areas and
   automatically adjusting the X-ray filter position to the determined X-ray filter positions to attenuate X-ray radiation un-attenuated by patient anatomy for individual steps of said series of pre-programmed steps, in response to data representing the determined different positions.

14. An X-ray imaging system for performing automated multi-step imaging of patient anatomy, comprising:
   at least one computer for automatically determining a series of pre-programmed steps comprising a plurality of incremental distances to be moved by an X-ray detector and X-ray emitter combination relative to a portion of patient anatomy in response to predetermined data;
   an X-ray filter automatically adjustable to attenuate X-ray radiation in response to a control signal;
   an X-ray filter controller for,
      determining one or more areas of the X-ray detector exposed to X-ray radiation un-attenuated by patient anatomy during an initialization X-ray exposure for individual steps of said series of pre-programmed steps and
      determining different X-ray filter positions for corresponding individual steps of said series of pre-programmed steps in response to the determined areas; and
   an X-ray imaging device for automatically moving the X-ray detector and X-ray emitter combination relative to patient anatomy in the series of pre-programmed steps, in response to data representing the determined series of pre-programmed steps and user command and adjusting the X-ray filter position via said control signal to the determined X-ray filter positions to attenuate X-ray radiation un-attenuated by patient anatomy for individual steps of said series of pre-programmed steps, in response to the determined filter positions.

15. A system according to claim 14, wherein
said predetermined data comprises,
   (a) a start position for X-ray imaging at a first location of a portion of patient anatomy and
   (b) an end position for X-ray imaging at a second location of a portion of patient anatomy.

16. A system according to claim 14, wherein
said predetermined data comprises,
   (i) selected start and end positions for X-ray imaging the length of a portion of patient anatomy,
   (ii) the length of said portion of patient anatomy imaged in an individual step and
   (iii) overlap length desired between successive X-ray images.

17. A system according to claim 14, wherein
said X-ray filter is located substantially close to said X-ray emitter to attenuate X-ray radiation from said X-ray emitter before it passes through a patient.

18. An X-ray imaging system for performing automated multi-step imaging of patient anatomy, comprising:
   an interface for storing data representing selected positions including, (a) a start position for X-ray imaging at a first location of a portion of patient anatomy and
(b) an end position for X-ray imaging at a second location of a portion of patient anatomy;

at least one computer for automatically determining a series of pre-programmed steps comprising a plurality of incremental distances to be moved by an X-ray detector and X-ray emitter combination relative to said portion of patient anatomy in response to,
  (i) the selected start and end positions,
  (ii) the length of said portion of patient anatomy imaged in an individual step and
  (iii) overlap length desired between successive X-ray images;

an X-ray filter automatically adjustable to attenuate X-ray radiation in response to a control signal;

an X-ray filter controller for,
  determining one or more areas of the X-ray detector exposed to X-ray radiation un-attenuated by patient anatomy during an initialization X-ray exposure for individual steps of said series of pre-programmed steps and
  determining different X-ray filter positions for corresponding individual steps of said series of pre-programmed steps in response to the determined areas; and an X-ray imaging device for automatically moving the X-ray detector and X-ray emitter combination relative to patient anatomy in the series of pre-programmed steps, in response to data representing the determined series of pre-programmed steps and user command and adjusting the X-ray filter position via said control signal to the determined X-ray filter positions to attenuate X-ray radiation un-attenuated by patient anatomy for individual steps of said series of pre-programmed steps, in response to the determined filter positions.

* * * * *